US012632090B2

(12) United States Patent
Hieb et al.

(10) Patent No.: US 12,632,090 B2
(45) Date of Patent: May 19, 2026

(54) FLOOR MOUNT FOR MEDICAL COMPUTER

(71) Applicant: Boston Scientific Scimed, Inc., Maple Grove, MN (US)

(72) Inventors: Lucas Hieb, Ham Lake, MN (US); Christopher John Sperry, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 105 days.

(21) Appl. No.: 18/529,319

(22) Filed: Dec. 5, 2023

(65) Prior Publication Data

US 2024/0184339 A1 Jun. 6, 2024

Related U.S. Application Data

(60) Provisional application No. 63/430,147, filed on Dec. 5, 2022.

(51) Int. Cl.
G06F 1/16 (2006.01)
G16H 40/63 (2018.01)

(52) U.S. Cl.
CPC ............. G06F 1/166 (2013.01); G16H 40/63 (2018.01)

(58) Field of Classification Search
CPC .... A47B 2200/0001; A47B 2200/0043; A47B 2200/0045; A47B 2200/0046; A47B 2200/80067; A47B 2200/0068; A47B 2097/003; A47B 81/00; G06F 1/1601; H05K 5/00; H05K 5/0004; H05K 5/0204; H05K 5/023

USPC ......................................................... 108/50.1
See application file for complete search history.

(56) References Cited

U.S. PATENT DOCUMENTS

| | | | | | |
|---|---|---|---|---|---|
| 591,504 | A | * | 10/1897 | Shaffer | A47B 27/02 |
| | | | | | 108/9 |
| 1,930,348 | A | * | 10/1933 | Parrott | A47B 43/02 |
| | | | | | 312/297 |
| 5,505,473 | A | * | 4/1996 | Radcliffe | B65G 1/1376 |
| | | | | | 340/8.1 |
| D404,875 | S | * | 1/1999 | Sandy | D34/21 |
| 5,957,059 | A | * | 9/1999 | Burhman | A47B 21/007 |
| | | | | | 108/50.01 |
| 8,066,242 | B2 | * | 11/2011 | Potter | H02G 3/26 |
| | | | | | 29/559 |

(Continued)

OTHER PUBLICATIONS

Alpha Park Public Library (Jul. 9, 2019), Slant-top table for sale 2 benches nest underneath table 78" long, 28" wide (image attached), Facebook. https://www.facebook.com/AlphaParkPublicLibrary/posts/slant-top-table-for-sale2-benches-nest-underneath-table78-long-28-wide25/10156474358276472. (Year: 2019).*

*Primary Examiner* — Cassandra Davis
(74) *Attorney, Agent, or Firm* — Seager, Tufte & Wickhem, LLP

(57) ABSTRACT

Floor mounts and/or floor mount enclosures for a medical computer are disclosed. An example floor mount may include an enclosure framework having a first base, a second base, and a top panel. The second base may be angled. A computer compartment may be defined adjacent the first base. The computer compartment may be configured to house a medical computer therein. An accessory compartment may be defined adjacent the second base. An arcuate rim may be disposed along an end region of the top panel.

18 Claims, 10 Drawing Sheets

(56) References Cited

U.S. PATENT DOCUMENTS

| D671,703 | S | * | 11/2012 | Guasta | ........................... | D34/19 |
| 8,320,110 | B2 | * | 11/2012 | Chen | ..................... | G06F 1/1632 |
| | | | | | | 235/462.46 |
| D708,809 | S | * | 7/2014 | Maddux | ......................... | D34/19 |
| 2008/0106173 | A1 | * | 5/2008 | Konopka | ................. | B65G 1/04 |
| | | | | | | 312/35 |
| 2008/0315734 | A1 | * | 12/2008 | Birsel | .................... | A47B 67/04 |
| | | | | | | 312/352 |
| 2014/0123882 | A1 | * | 5/2014 | Kassanoff | ............ | A47B 87/002 |
| | | | | | | 108/26 |

* cited by examiner

FLOOR MOUNT FOR MEDICAL COMPUTER

CROSS-REFERENCE TO RELATED APPLICATIONS

This application claims the benefit of priority under 35 U.S.C. § 119 of U.S. Provisional Application No. 63/430, 147, filed Dec. 5, 2022, the entire disclosure of which is hereby incorporated by reference.

TECHNICAL FIELD

The present disclosure pertains to medical devices, and methods for manufacturing medical devices. More particularly, the present disclosure pertains to floor mounts for medical computers.

BACKGROUND

A wide variety of medical devices have been developed for medical use, for example, intravascular use. Some of these devices include guidewires, catheters, and the like. In some instances, these devices may be used with a medical computer. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A floor mount for a medical computer is disclosed. The floor mount comprises: an enclosure framework having a first base, a second base, and a top panel; wherein the second base is angled; wherein a computer compartment is defined adjacent the first base, the computer compartment being configured to house a medical computer therein; wherein an accessory compartment is defined adjacent the second base; and wherein an arcuate rim is disposed along an end region of the top panel.

Alternatively or additionally to any of the embodiments above, the first base has a plurality of apertures formed therein.

Alternatively or additionally to any of the embodiments above, the enclosure framework includes a number of flanges.

Alternatively or additionally to any of the embodiments above, the enclosure framework includes a cord management member.

Alternatively or additionally to any of the embodiments above, a handle is disposed along the top panel.

Alternatively or additionally to any of the embodiments above, the enclosure framework is formed from a plurality of separate panels.

Alternatively or additionally to any of the embodiments above, the enclosure framework is formed from a singular panel that is formed into the enclosure framework.

Alternatively or additionally to any of the embodiments above, the enclosure framework includes a second accessory compartment.

Alternatively or additionally to any of the embodiments above, the accessory compartment includes a side opening.

Alternatively or additionally to any of the embodiments above, the accessory compartment includes a top opening.

Alternatively or additionally to any of the embodiments above, the top panel includes a first angled region and a second angled region.

Alternatively or additionally to any of the embodiments above, further comprising a second top panel having a second arcuate rim.

Alternatively or additionally to any of the embodiments above, one or more securing members are disposed along the first base.

A floor mount enclosure for a medical computer is disclosed. The floor mount enclosure comprises: an enclosure framework including a first base having a plurality of apertures formed therein, an angled second base, and a top panel; wherein a computer compartment is defined within the enclosure framework adjacent the first base, the computer compartment being configured to have a medical computer disposed therein; and wherein an accessory compartment is defined within the enclosure framework adjacent the angled second base.

Alternatively or additionally to any of the embodiments above, an arcuate rim is disposed along an end region of the top panel.

Alternatively or additionally to any of the embodiments above, the enclosure framework includes a number of flanges.

Alternatively or additionally to any of the embodiments above, the enclosure framework includes a cord management member.

Alternatively or additionally to any of the embodiments above, one or more securing members are disposed along the first base.

Alternatively or additionally to any of the embodiments above, the accessory compartment includes a side opening.

A floor mount for a medical computer is disclosed. The floor mount comprises: an enclosure framework including a first base having a plurality of apertures formed therein, an angled second base disposed above the first base, and a top panel having an arcuate rim disposed at and end region thereof; one or more cord managing members coupled to the enclosure framework; one or more securing members disposed along the first base; wherein a computer compartment is defined within the enclosure framework adjacent the first base, the computer compartment being configured to have a medical computer disposed therein; and wherein an accessory compartment is defined within the enclosure framework adjacent the angled second base.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
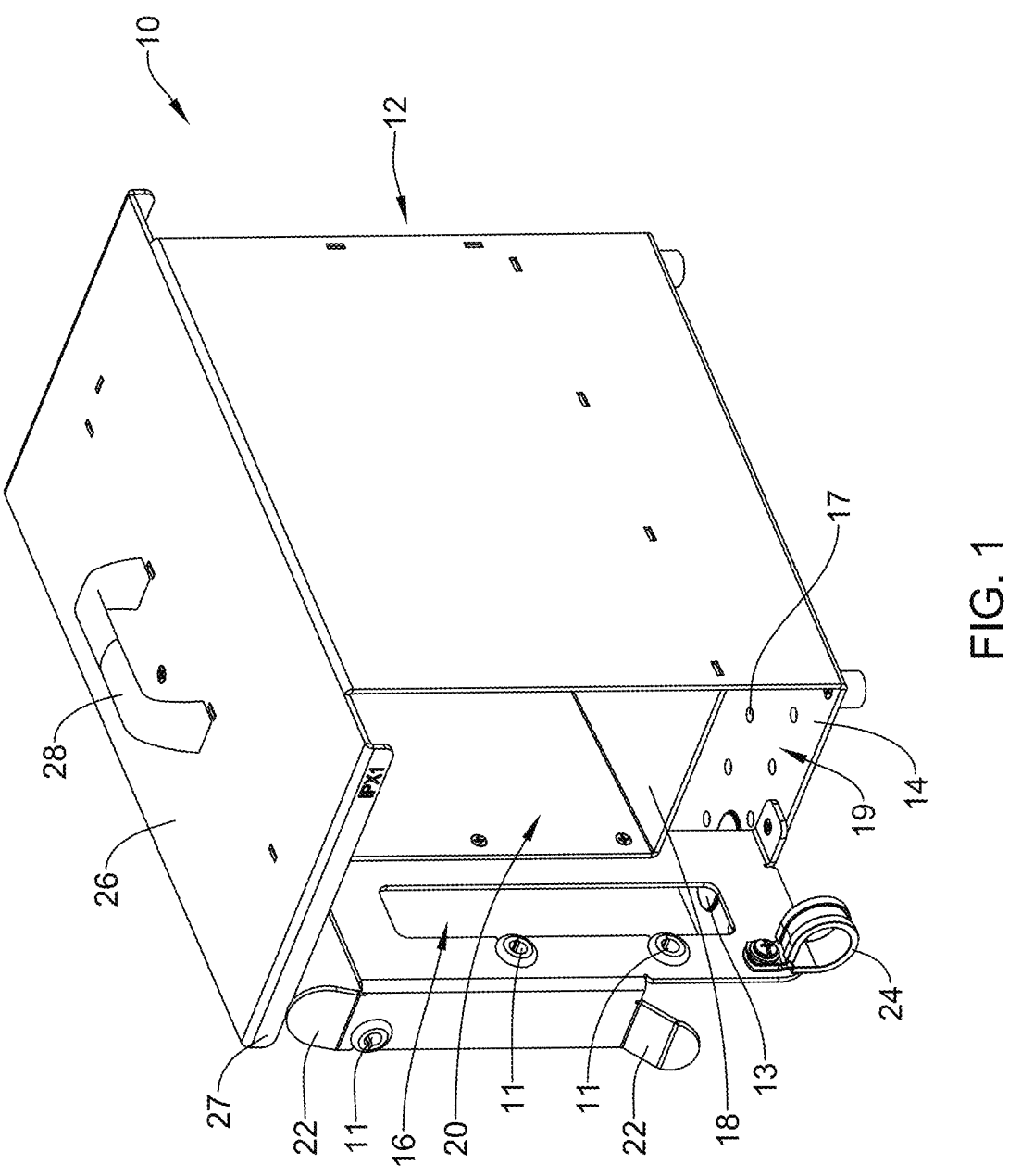
FIG. 1 is a perspective view of an example floor mount enclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Current health care facilities utilize a number of different medical devices and systems. Some of the systems include computers that aid in various interventions. For example, systems like intravascular ultrasound (IVUS) systems may include an IVUS catheter, various tools that work with the catheter, and a computer. It can be appreciated that some of the systems and/or components of the systems may be capital equipment that is used a number of different times and with a number of different patients. Thus, some systems may utilize a medical cart or the like for these components. Other systems may mount or locate components such as medical computers along the floor of the room. For example, a computer for use with and IVUS system may be disposed in a floor enclosure. Disclosed herein are enclosures that may be used to house a medical computer for use and/or storage along the floor. Furthermore, the enclosure may include a number of structural features that help improve efficiency of the system, help to shield the computer from fluids, and offer convenient access for cords, cables, accessories, and the like.

Figure 2:
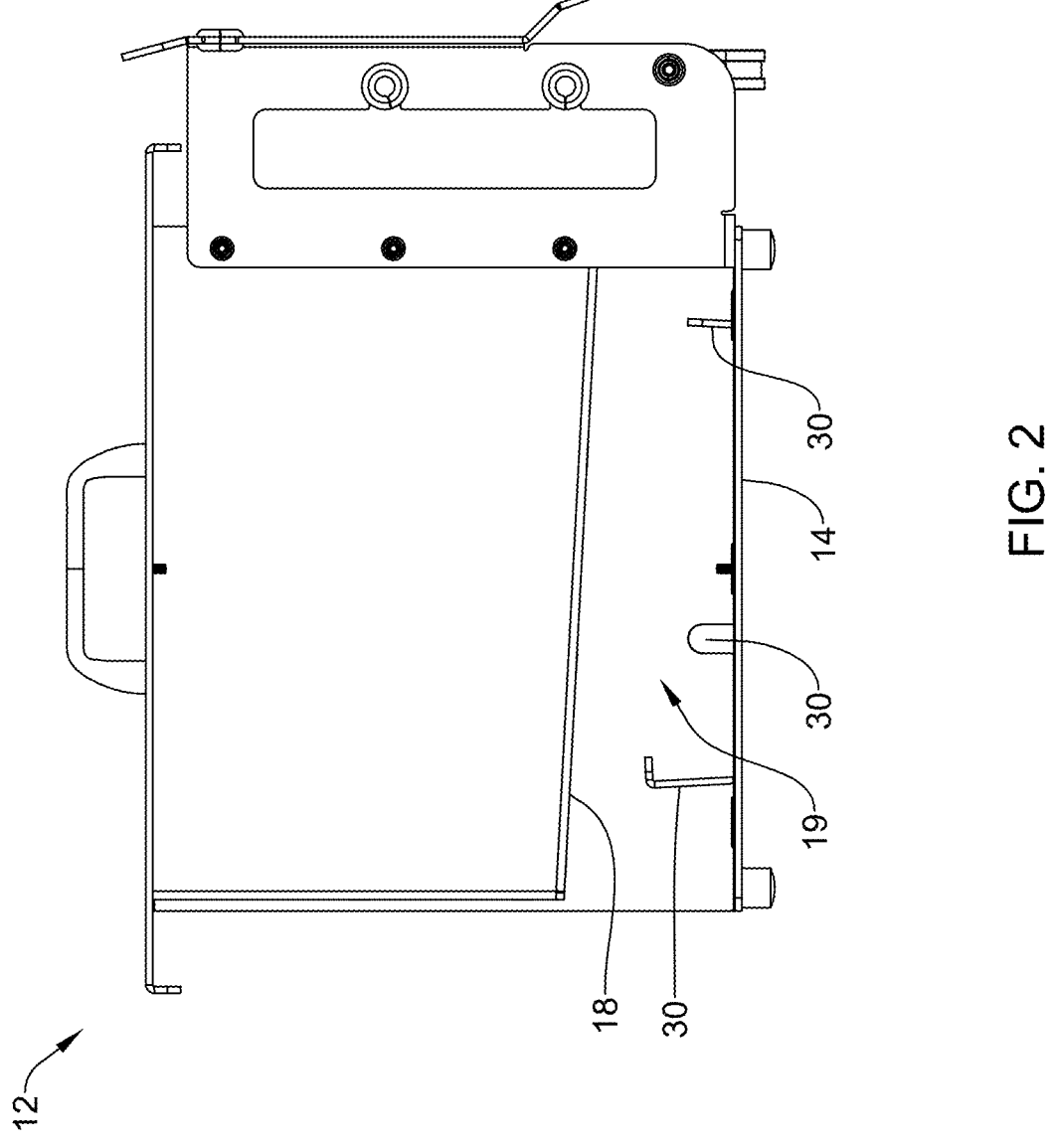
FIG. 2 is a side view of an example floor mount enclosure.
Figure 3:
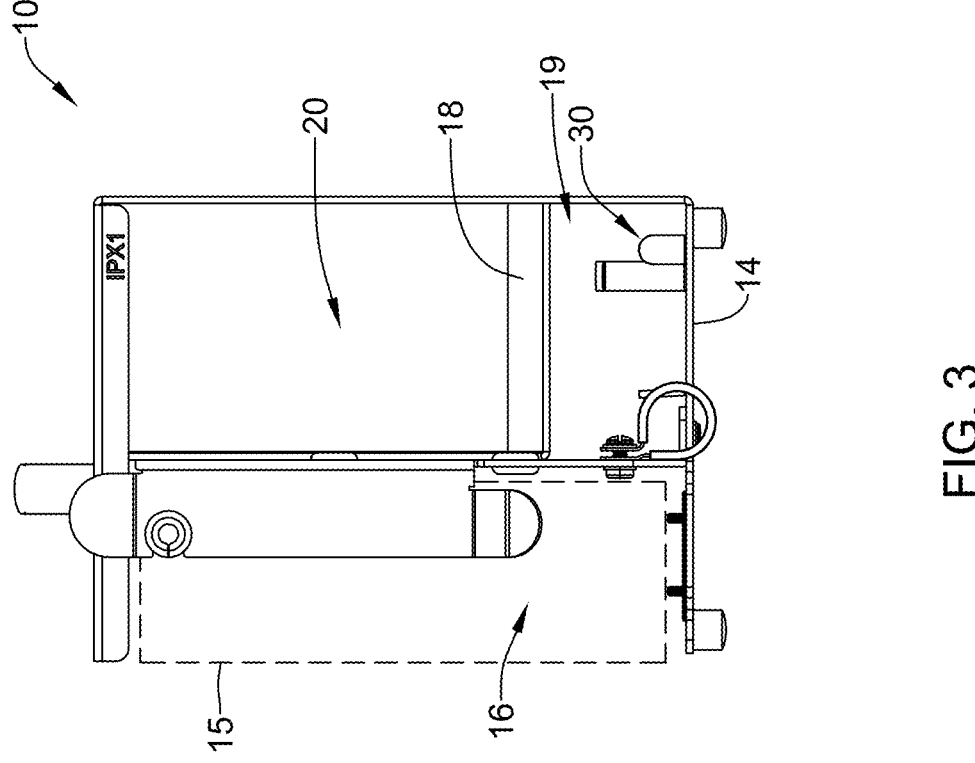
FIG. 3 is an end view of an example floor mount enclosure.

FIGS. 1-3 illustrates a floor mount enclosure 10. In general, the floor mount enclosure 10 may be used to store a medical computer and/or accessories/tools for use therewith in a convenient, protective, and portable enclosure. While use/storage along the floor may be accomplished by the floor mount enclosure 10, some floor mount enclosures contemplated may include mounting structures that allow the floor mount enclosure 10 to be mounted to a cart, bed rail, or the like.

The floor mount enclosure 10 may include an enclosure framework 12. The enclosure framework 12 may have a first platform or base 14. A computer compartment 16 (e.g., see also FIG. 3 for another view that depicts the location of the computer compartment 16) may be defined adjacent the first base 14. For example, the computer compartment 16 may be suitably sized and/or arranged to accommodate a medical computer (e.g., a medical computer 15 as schematically depicted in FIG. 3), for example along the first base 14. The medical computer may be disposed along the first base 14 from the side or end of the enclosure framework 12. The computer compartment 16 may large enough to hold the medical computer, allow for cords to be disposed adjacent to the medical computer, allow for indicator lights on the medical computer to be seen/visualized by a user, and/or provide additional desirable features. In some instances, the first base 14 may have a number of openings or apertures 17 formed therein. The openings 17 may be configured to allow for circulation of air about the medical computer. In addition, the openings 17 may allow for any fluids that may enter the computer compartment 16 to pass therethrough.

The enclosure framework 12 may have a second platform or base 18. In at least some instances, the second base 18 may be disposed above the first base 14. Other arrangements (e.g., below the first base 14, along the side of the first base 14, etc.) are contemplated. A tool and/or accessory compartment 20 may be defined adjacent the second base 18. The accessory compartment 20 may be suitably sized and/or arranged to accommodate tools/accessories for use with the medical computer during an intervention. For example, if the intervention includes an IVUS imaging procedure, accessories such as a motor drive unit, pull-back sled, cables including power cables, etc. may be housed in the accessory compartment 20. The arrangement of the enclosure framework 12 may allow for tools/accessories to be disposed along the second base 18 from the side or end of the enclosure framework 12. In other words, the accessory compartment 20 may have a side or end opening that opens into the accessory compartment 20. In at least some instances, a power supply compartment 19 may be defined underneath the accessory compartment 20 and beside/adjacent the computer compartment 16.

The enclosure framework 12 may include a number of hooks and/or flange members such as flanges 22. In at least some instances, the flanges 22 may be used as substrates for wrapping cords/cables thereon. Other uses are contemplated. In addition, the enclosure framework 12 may include a cord management member 24. The cord management member 24 may include a loop that can be opened to place cords therein and the closed back into a loop configuration. In some instances, the cord management member 24 may be a hook and loop strap. The enclosure framework 12 may include one or more cable guards 11. In at least some instances, the cable guards 11 may take the form of grommets (e.g., rubber grommets) that allow for cables to be secured to the enclosure framework 12 and may also help to protect the cables from unintended disconnect and/or damage.

Figure 1A:
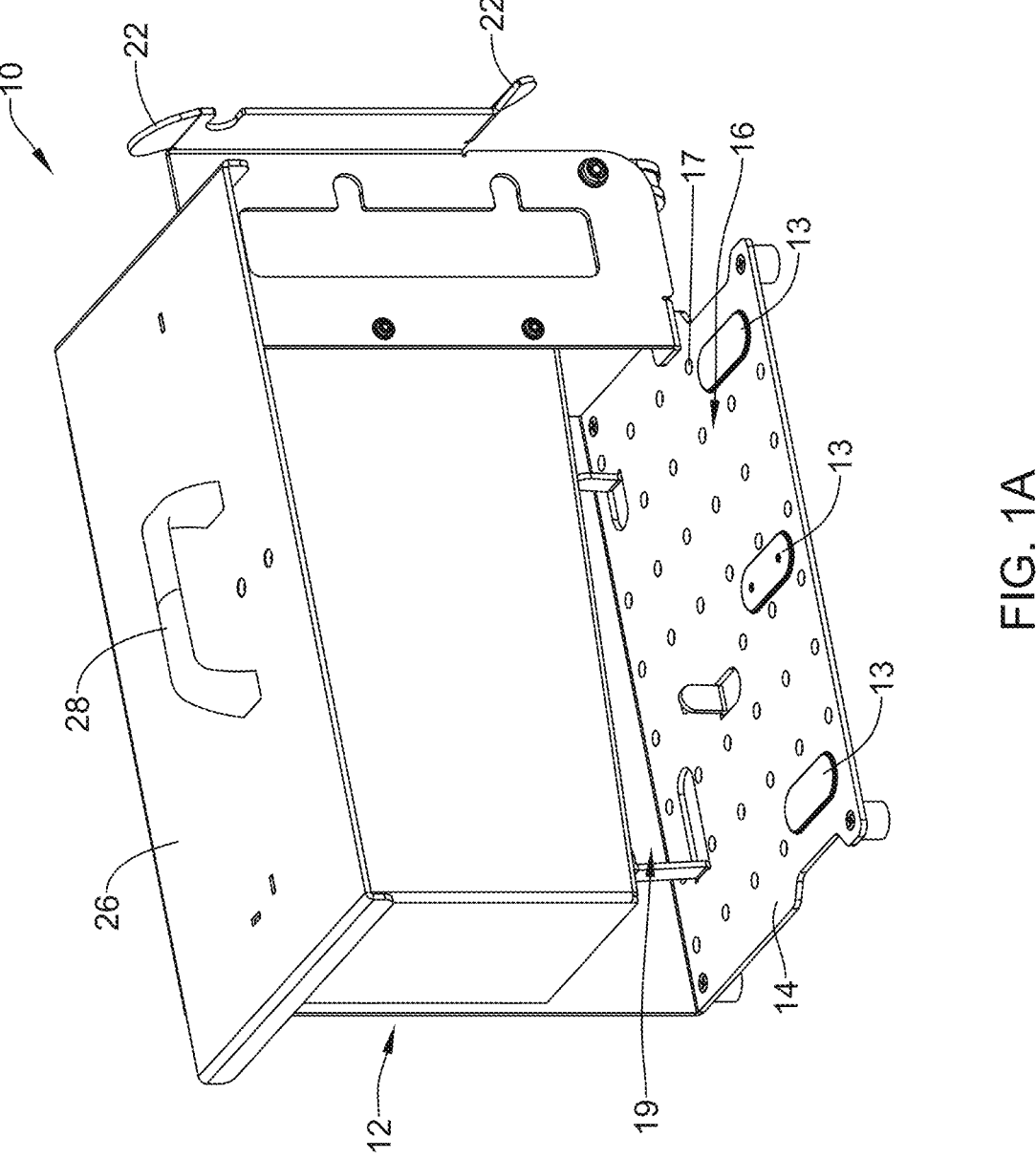
FIG. 1A depicts a portion of an example floor mount enclosure.

In at least some instances, the first base 14 (e.g., adjacent to the computer compartment 16) may include one or more raised surfaces 13. The raised surfaces 13 may help to raise the medical computer away from the first base 14. This may help to reduce/prevent capillary action from pulling liquid in-between the first base 14 and the computer. FIG. 1A shows the first base 14 with other structures of the enclosure framework 12 removed so that the raised surfaces 13 can be more clearly seen. In some instances, the raised surfaces 13 may project upward from the first base 14. In some of these and in other instances, the raised surfaces 13 may project (e.g., downward) along the bottom of the first base 14.

The enclosure framework 12 may include a top panel 26. In some instances, the top panel 26 may be angled or pitched (e.g., relative to the ground and/or the first base 14) so that the top panel 26 may help to divert fluids away from the enclosure framework 12. This may resemble the angle or pitch of a typical roof or similar structure designed to divert fluid away from the enclosure framework 12. In some instances, the top panel 26 may be disposed at an angle of 1-60 degrees, or about 1-45 degrees, or about 5-30 degrees, or about 15 degrees. In some of these and in other instances, a curved or arcuate lip or rim 27 may be disposed along and end region of the top panel 26. In general, the arrangement of the top panel 26 and the rim 27 may be configured so that fluids contacting the top panel 26 are diverted away from the computer compartment 16 and/or the accessory compartment 20. The angle or orientation of the rim 27 may help to reduce the likelihood that fluids could drip onto the first base 14 and/or the second base. A handle 28 may be disposed along the top panel 26. The handle 28 may be used to help transport the floor mount enclosure 10 from one location to another.

FIGS. 2-3 are partially cutaway side and end views of the enclosure framework 12. Here it can be seen that the second base 18 may be angled or pitched. The angled arrangement of the second base 18 may help to divert fluids disposed along the second base 18 (and/or entering the accessory compartment 20 in general) away from the enclosure framework 12. The angle of the second base 18 may resemble the angle or pitch of a typical roof or similar structure designed to divert fluid away from the enclosure framework 12. In some instances, the second base 18 may be disposed at an angle of 5-60 degrees, or about 15-60 degrees, or about 30-60 degrees, or about 45 degrees. These are just examples. Other angles are contemplated. The angle may be measured with respect to the ground (e.g., horizontal) and/or the first base 14.

The first base 14 may include one or more securing members 30 for securing a power supply along the first base 14. The securing members 30 may take the form of clips or dividers that allow for the power supply to be disposed along the first base 14 and be held relatively stationary relative thereto. In some instances, the securing members 30 may be detachably coupled to the first base 14. This may allow for the securing members 30 to be moved to accommodate differently sized power supplies.

Figure 4:
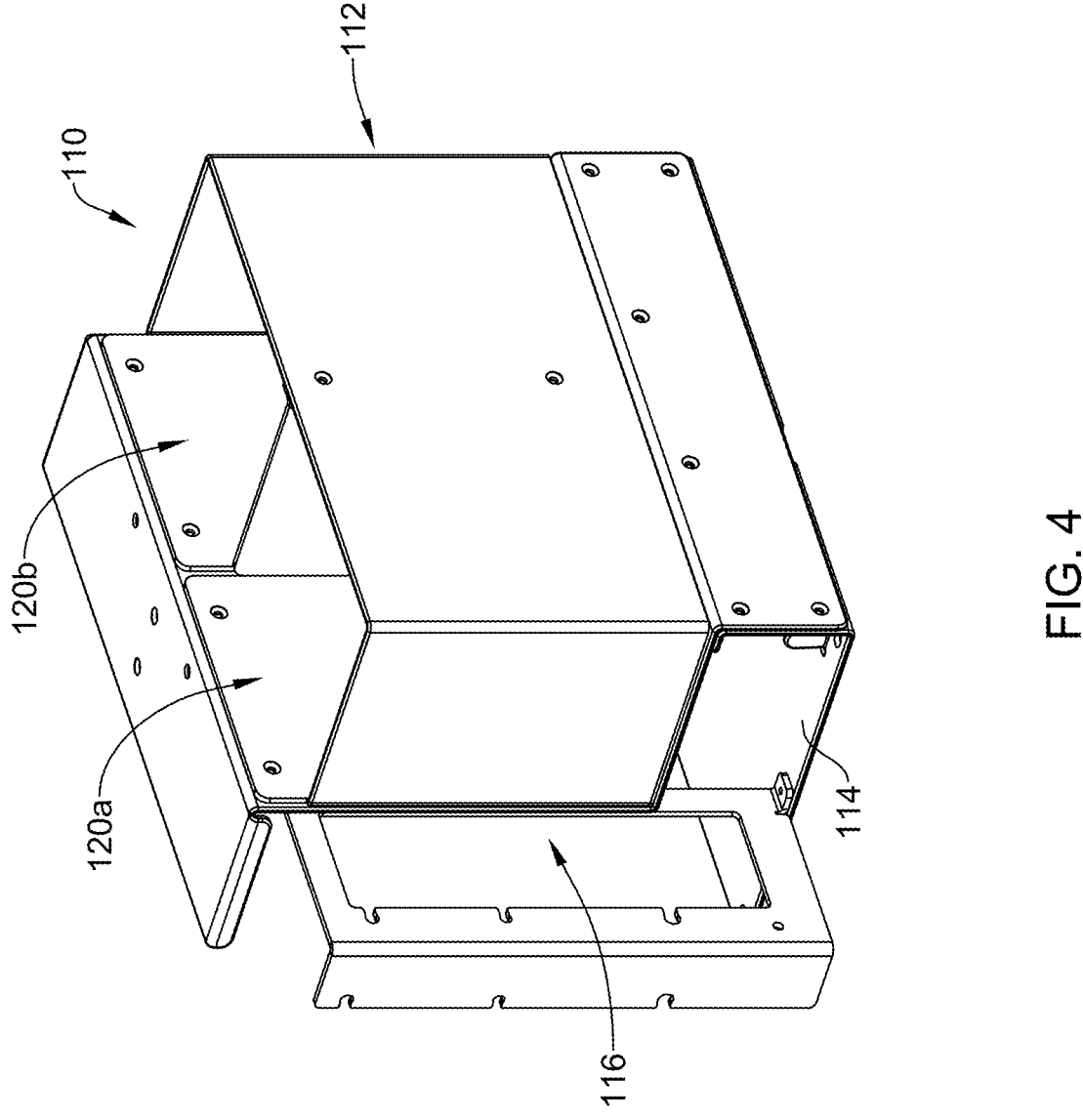
FIG. 4 is a perspective view of a portion of an example floor mount enclosure.

FIG. 4 illustrates a portion of another example floor mount 110 that may be similar in form and function to other floor mounts disclosed herein. The floor mount 110 may include an enclosure framework 112. The enclosure framework 112 may include a first base 114. A computer compartment 116 may be defined along/adjacent the first base 114. While the accessory compartment 20 of the enclosure framework 12 may have a side or end opening that opens into the accessory compartment 20, the enclosure framework 112 may be understood to have a top opening that opens into one or more tool/accessory compartments including compartments such as the tool/accessory compartments 120a, 120b.

Figure 5:
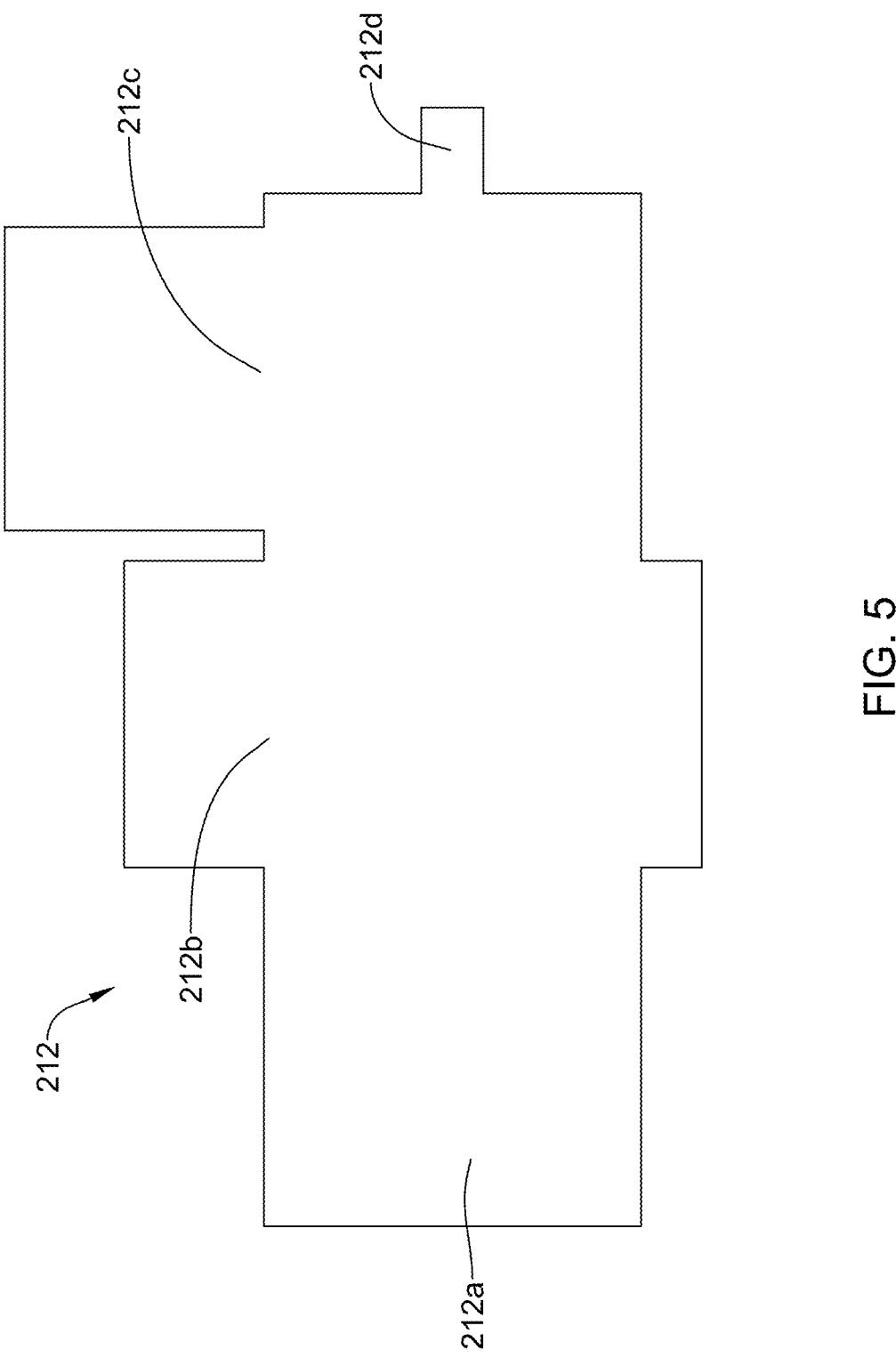
FIG. 5 schematically depicts an example enclosure framework.
Figure 6:
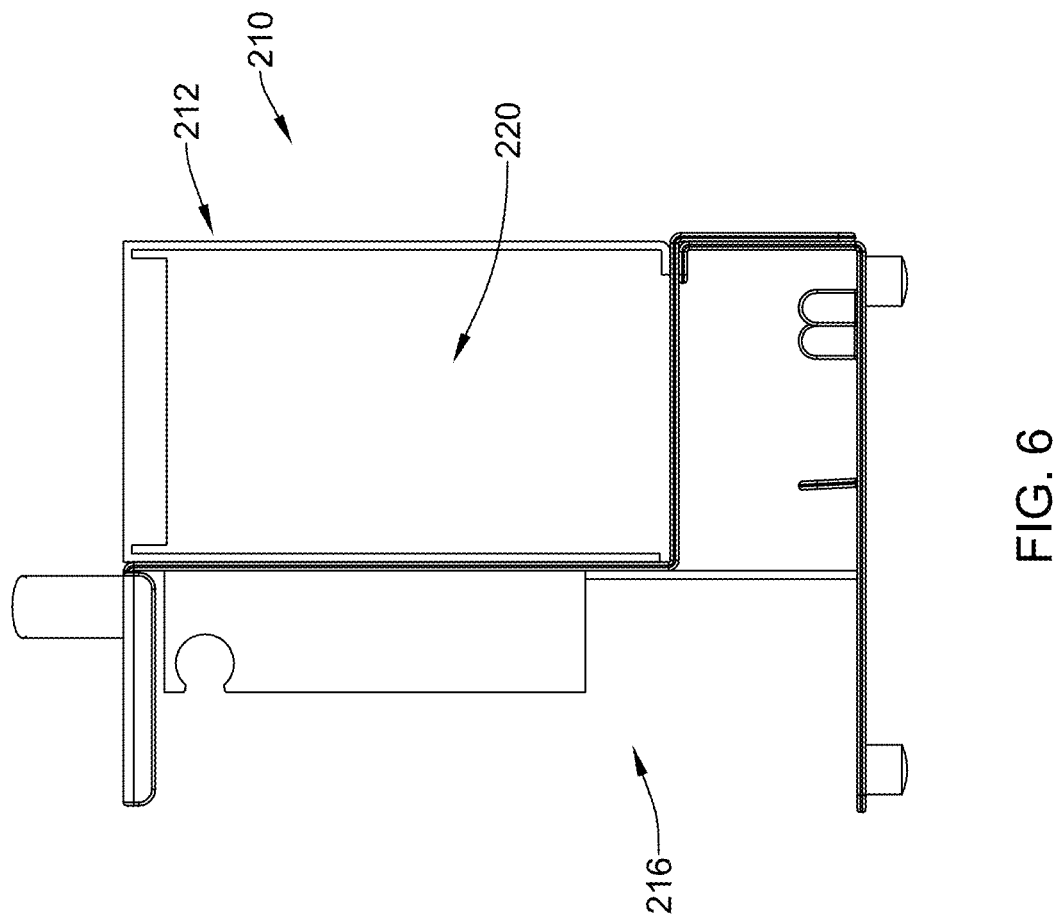
FIG. 6 is an end view of a portion of an example floor mount enclosure.

FIGS. 5-6 schematically illustrate another example enclosure framework 212 that may be similar in form and function to other enclosures disclosed herein. Rather than being formed as an assembly of different panels secured together, the enclosure framework 212 may be formed from a singular panel having a number of sections, for example section 212a, 212b, 212c, 212d. The sections 212a, 212b, 212c, 212d may be folded or otherwise arranged into the enclosure framework 212 (e.g., which may be part of an example floor mount assembly 210). When suitably configured, the enclosure framework 212 may define a computer compartment 216 and a tool/accessory compartment 220 (e.g. as depicted in FIG. 6).

Figure 7:
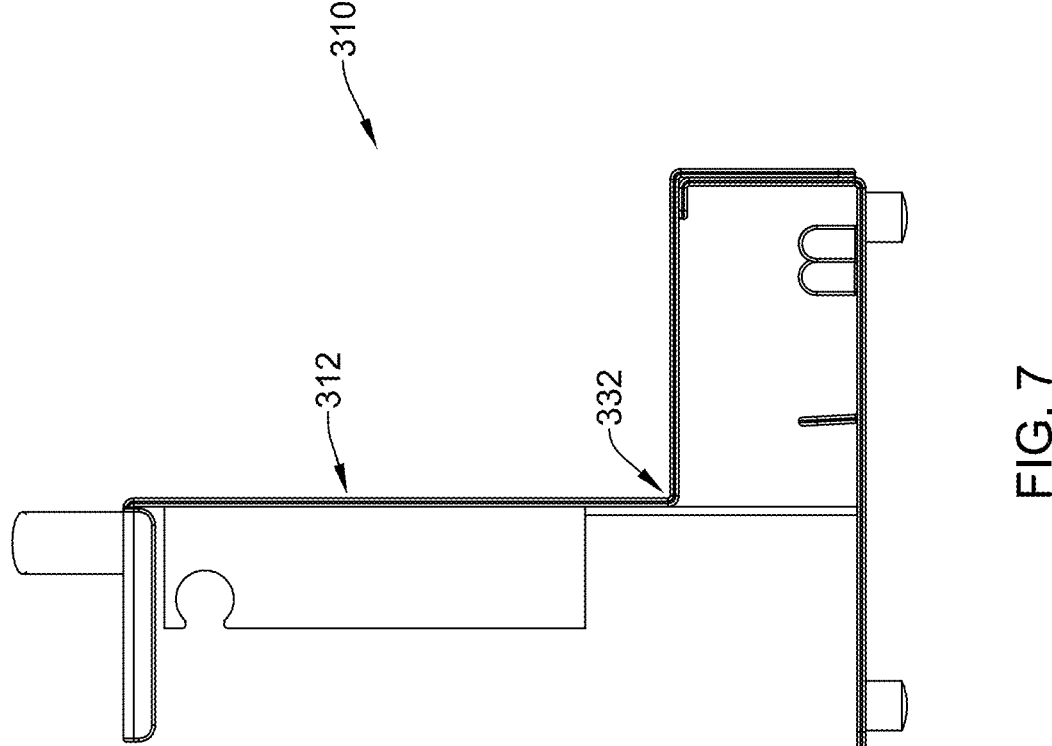
FIG. 7 is an end view of a portion of an example floor mount enclosure.

FIG. 7 schematically illustrates a portion of another example floor mount assembly 310 that may be similar in form and function to other floor mount assemblies disclosed herein. The floor mount assembly 310 may include an enclosure framework 312. The enclosure framework 312 may include a pivoting panel that pivots about a pivot point 332. The pivoting arrangement may help to protect tools/accessories underneath.

Figure 8:
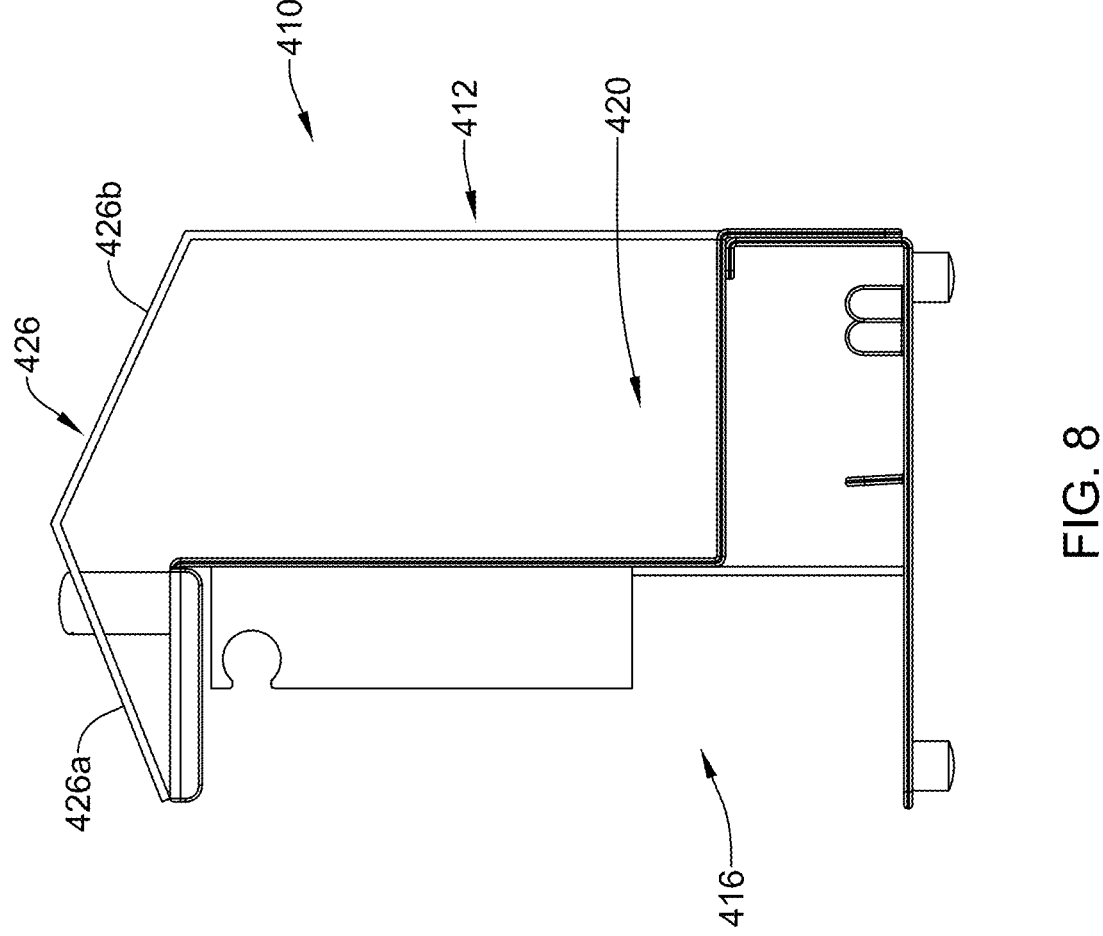
FIG. 8 is an end view of a portion of an example floor mount enclosure.

FIG. 8 schematically illustrates a portion of another example floor mount assembly 410 that may be similar in form and function to other floor mount assemblies disclosed herein. The floor mount assembly 410 may include an enclosure framework 412. The enclosure framework 412 may define a computer compartment 416 and a tool/accessory compartment 420. The enclosure framework 412 may include an angled or tented top panel 426. The top panel 426 may include a first angled region 426a and a second angled region 426b. Much like other top panels disclosed herein, the top panel 426 is designed to help divert fluids away from the enclosure framework 412.

Figure 9:
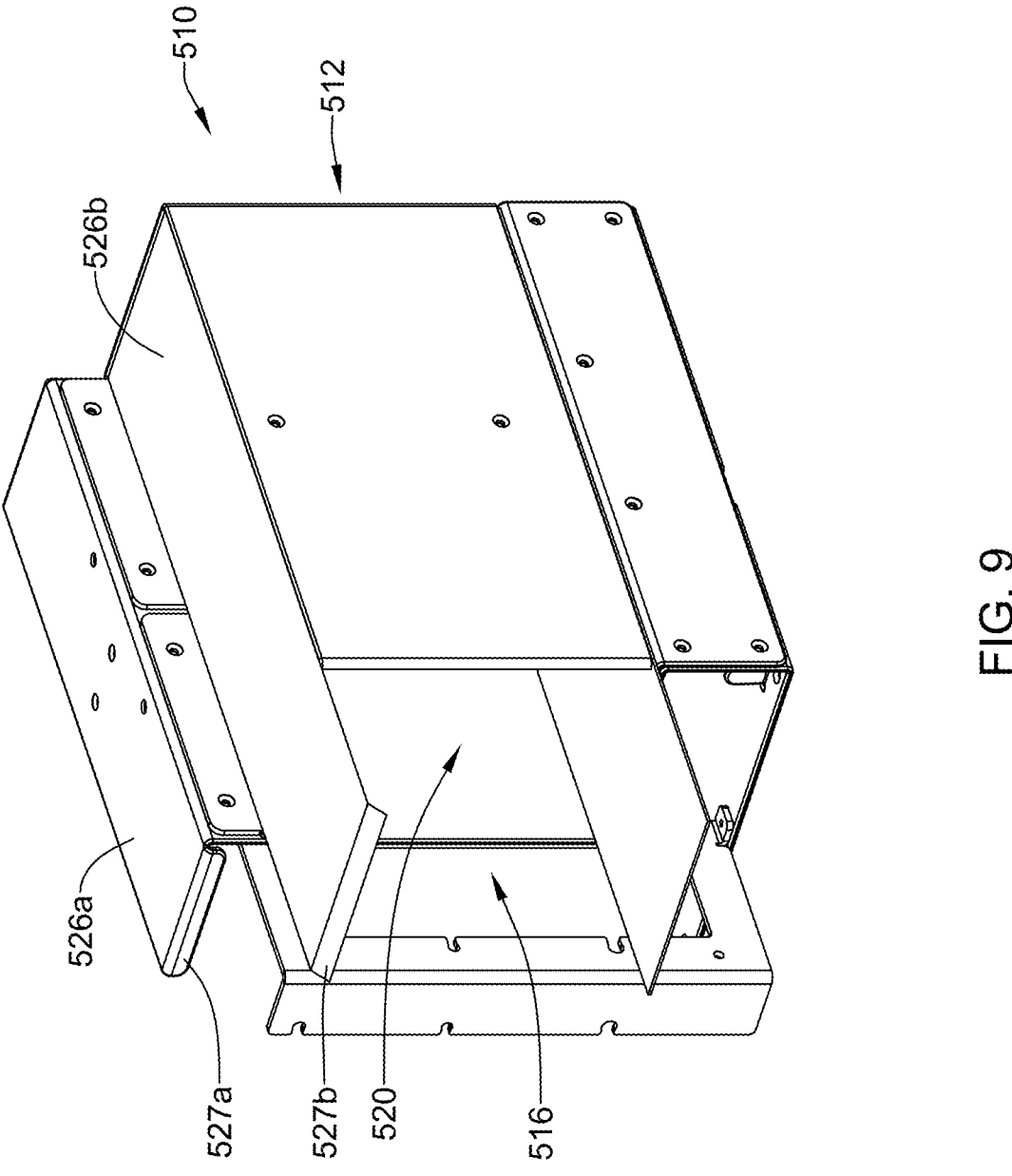
FIG. 9 is a perspective view of a portion of an example floor mount enclosure.

FIG. 9 schematically illustrates a portion of another example floor mount assembly 510 that may be similar in form and function to other floor mount assemblies disclosed herein. The floor mount assembly 510 may include an enclosure framework 512. The enclosure framework 512 may define a computer compartment 516 and a tool/accessory compartment 520. The enclosure framework 512 may include a first top portion 526a and a second top portion 526b. The first top portion 526a may include a first rim 527a. The first top portion 526a and/or the first rim 527a may help to divert fluids away from the enclosure framework 512 including diverting fluids away from the computer compartment 516, the accessory compartment 520, or both. The second top portion 526b may include a second rim 527b. Much like the first top portion 526a, second top portion 526b and/or the second rim 527b may help to divert fluids away from the enclosure framework 512 including diverting fluids away from the computer compartment 516, the accessory compartment 520, or both.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A floor mount for a medical computer, the floor mount comprising:

an enclosure framework having a first base, a second base, and a top panel;

wherein a computer compartment is defined adjacent the first base, the computer compartment being configured to house a medical computer therein;

wherein an accessory compartment is defined adjacent the second base;

wherein an arcuate rim is disposed along an end region of the top panel to divert fluids away from the enclosure framework; and wherein the second base is angled downward toward a side opening of the accessory compartment to divert fluid out of the side opening of the accessory compartment.

2. The floor mount of claim 1, wherein the first base has a plurality of apertures formed therein.

3. The floor mount of claim 1, wherein the enclosure framework includes a one or more flanges.

4. The floor mount of claim 1, wherein the enclosure framework includes a cord management member, one or more cable guards, or combinations thereof.

5. The floor mount of claim 1, wherein a handle is disposed along the top panel.

6. The floor mount of claim 1, wherein the enclosure framework is formed from a plurality of separate panels.

7. The floor mount of claim 1, wherein the enclosure framework is formed from a singular panel that is formed into the enclosure framework.

8. The floor mount of claim 1, wherein the enclosure framework includes a second accessory compartment.

9. The floor mount of claim 1, wherein the accessory compartment includes a top opening.

10. The floor mount of claim 1, wherein the top panel includes a first angled region and a second angled region.

11. The floor mount of claim 1, further comprising a second top panel having a second arcuate rim.

12. The floor mount of claim 1, wherein one or more securing members are disposed along the first base.

13. A floor mount enclosure for a medical computer, the floor mount enclosure comprising:

an enclosure framework including a first base having a plurality of apertures formed therein, an angled second base, and a top panel having a first angled region, a second angled region, and an arcuate rim disposed along an end region of the top panel that is configured to divert fluid from the top panel;

wherein a computer compartment is defined within the enclosure framework adjacent the first base, the computer compartment being configured to have a medical computer disposed therein;

wherein an accessory compartment is defined within the enclosure framework adjacent the angled second base;

wherein the second base is angled downward toward a side opening of the accessory compartment to divert fluid out of the side opening of the accessory compartment; and wherein the first base includes raised surfaces to prevent capillary action.

14. The floor mount enclosure of claim 13, wherein an arcuate rim is disposed along an end region of the top panel.

15. The floor mount enclosure of claim 13, wherein the enclosure framework includes one or more flanges.

16. The floor mount enclosure of claim 13, wherein the enclosure framework includes a cord management member, one or more cable guards, or combinations thereof.

17. The floor mount enclosure of claim 13, wherein one or more securing members are disposed along the first base.

18. A floor mount for a medical computer, the floor mount comprising:

an enclosure framework including a first base having a plurality of apertures formed therein and raised surfaces to prevent capillary action, an angled second base disposed above the first base, and a top panel having a first angled region, a second angled region, and an arcuate rim disposed along an end region of the top panel that is configured to divert fluid from the top panel;

one or more cord managing members coupled to the enclosure framework;

one or more securing members disposed along the first base;

wherein a computer compartment is defined within the enclosure framework adjacent the first base, the computer compartment being configured to have a medical computer disposed therein; and wherein an accessory compartment is defined within the enclosure framework adjacent the angled second base; and wherein the second base is angled downward toward a side opening of the accessory compartment to divert fluid out of the side opening of the accessory compartment.

* * * * *